United States Patent [19]

Kelly-Fry et al.

[11] 4,347,850
[45] Sep. 7, 1982

[54] DIRECT WATER COUPLING DEVICE FOR ULTRASOUND BREAST SCANNING IN A SUPINE POSITION

[75] Inventors: Elizabeth Kelly-Fry; Francis J. Fry; George W. Gardner, all of Indianapolis, Ind.

[73] Assignee: Indianapolis Center for Advanced Research, Inc., Indianapolis, Ind.

[21] Appl. No.: 131,669

[22] Filed: Mar. 19, 1980

[51] Int. Cl.³ .............................................. A61B 10/00
[52] U.S. Cl. ..................................................... 128/660
[58] Field of Search ................................. 128/660–663, 128/65–66, 130, 365, 370, 280–282; 73/597, 602, 626, 644; 250/363 S, 445 T, 456

[56] References Cited

U.S. PATENT DOCUMENTS

| | | | |
|---|---|---|---|
| 1,775,442 | 9/1930 | Sarason | 128/370 |
| 2,244,973 | 6/1941 | Swan | 128/28 |
| 2,435,894 | 2/1948 | Marc-Aurele | 128/65 |
| 2,730,104 | 1/1956 | Newman | 128/370 |
| 3,167,070 | 1/1965 | Silverman | 128/206.24 |
| 3,237,623 | 3/1966 | Gordon | 128/24 |
| 3,480,002 | 11/1969 | Flaherty et al. | 128/660 |
| 3,821,891 | 7/1974 | Collins et al. | 128/660 X |
| 3,963,933 | 6/1976 | Heukes, Jr. | 250/456 |
| 4,130,112 | 12/1978 | Frazer | 128/660 |
| 4,206,763 | 6/1980 | Pedersen | 128/660 |

OTHER PUBLICATIONS

Fry, F. J., "Precision Hi-Intensity Focusing UTS Machines for Surgery", Amer. Jrnl. Phys. Medicine, vol. 37, No. 3, Jun. 1958.
Fry, W. J. et al., "Fundamental Neurol. Resrch. and Human Neurosurg. Using Intense Ultrasound, " IRE trans. on Med. Electron., vol. ME-7, Jul. 1960.
Kelly-Fry, E., et al., "Pot. for UTS Visualization for Det. Abnormal Structures Within Female Breast", 1972, IEEE UTS Symp. Proc., 10/4/72-10/7/72, Boston, Mass.
Jellins, J. et al., "UTS Visualization of the Breast", Med. Jrnl. of Australia, Feb. 6, 1971, pp. 305–309.

*Primary Examiner*—Kyle L. Howell
*Assistant Examiner*—Francis J. Jaworski
*Attorney, Agent, or Firm*—Woodard, Weikart, Emhardt & Naughton

[57] ABSTRACT

A direct water coupling device for ultrasound scanning of the human breast in a supine position. A tank, which has an open top and an open bottom and has a bottom edge which is shaped so as to conform to the shape of a human body about the perimeter of the breast area, is placed in a sealed position about the breast while the patient is in a supine position. A strapping apparatus maintains the device in position while the tank is filled with water and the ultrasound scan is performed.

7 Claims, 3 Drawing Figures

DIRECT WATER COUPLING DEVICE FOR ULTRASOUND BREAST SCANNING IN A SUPINE POSITION

BACKGROUND OF THE INVENTION

1. Field of the Invention

The field of the invention is acoustical coupling devices for ultrasound scanning of the human breast.

2. Description of the Prior Art

When applying ultrasonic visualization instrumentation, it is typically necessary to use a coupling agent between the transducer emitting the high frequency sound wave and the skin surface of the patient. The coupling medium acts as a transport medium for the sound waves and should match as closely as possible, the acoustic impedance of the skin. Liquids, and in particular, water are typically used as coupling agents because of their ready availability and acoustic properties.

Breast scanning has been performed with the use of an indirect coupling agent such as a "water bag". In this type of technique a so called "bag" (a flexible container which molds to the skin surface) of water is placed against the breast of the patient and the transducer is placed or permanently located within either an open or closed water bag. There are several disadvantages of the standard water bag technique in relation to its use with ultrasound breast scanning. These disadvantages include (1) the trapping of air between the bag surface and the skin which impedes the transmission of the sound waves; (2) potential failure of tumor detection due to displacement of the tumor mass from its original position caused by pressure of the water bag; (3) inability to verify tumor location by manually palpating the breast; and (4) potential failure to detect subtle alterations in structural components of the breast tissue (which are the earliest sign of breast cancer) because of alterations in the structural architecture resulting from the "water bag" pressure.

Devices are currently being used which provide for direct water coupling of the human breast with the patient in either a prone or a sitting forward position. In these techniques, the breast is allowed to float in the liquid environment and thus inaccuracies due to pressures caused by a water bag are alleviated. However, the techniques of direct water coupling with the patient in a sitting forward or prone position present a disadvantage in that during the scanning procedure the breast area is not readily accessible to a technician and thus repalpation of the breast and the making of fine adjustments in the scan are difficult and awkward to perform. U.S. Pat. No. 3,480,002 to Flaherty et al. discloses the above mentioned ultrasound scanning techniques of using a water bag and of utilizing direct water coupling for an ultrasound scan performed with the patient in a prone position.

SUMMARY OF THE INVENTION

There are a number of advantages to direct water coupling in the supine position, namely, (1) during the scanning procedure the breast surface is readily accessible to a medical technician or physician so that repalpation of the breast to recheck or doubtful finding is possible without removing the patient from the apparatus; (2) the patient's position can be easily adjusted in respect to placing their weight either primarily on their back or partially on their shoulder for the purpose of achieving the best angle of incidence of the sound beam in respect to the breast surface, and to prevent total loss of the sound beam at the outer curved surface of the breast due to its reflection away from this breast surface because of its so-called "critical angle" of entrance. Failure of the sound beam to penetrate the outermost, lateral regions of the breast because of the sound beam hitting these surfaces at the critical angle is a common phenomenon in the prone or sitting forward position; (3) it is possible to recheck the position of a palpable tumor or other overt pathology during the scanning process in order to be certain that the complete volume of the tumor mass is being imaged and (4) the supine position is the most comfortable position for patients of all ages and states of health.

The present invention relates to coupling devices for ultrasound breast scanning in a supine position. In one embodiment, a tank has an open top and an open bottom, with the bottom edge of the tank being shaped so as to conform to the shape of a human body about the perimeter of a breast area. Inflatable latex tubing sealing means at the bottom edge of the tank prevents leakage when the device is in position. Straps are connected to the tank and wrap around the body of the patient to provide a means of applying pressure and supporting the device when it is in position about the patient.

It is an object of the present invention to provide an improved direct water coupler which is useful for ultrasound breast scanning in a supine position.

It is a further object to provide such a coupler which can be used simply and quickly in a clinical environment.

It is a further object to provide such a coupler which is comfortable to the patient.

These and other objects and advantages will become apparent in the following drawings and description of the preferred embodiment.

DESCRIPTION OF THE PREFERRED EMBODIMENT

Figure 1:
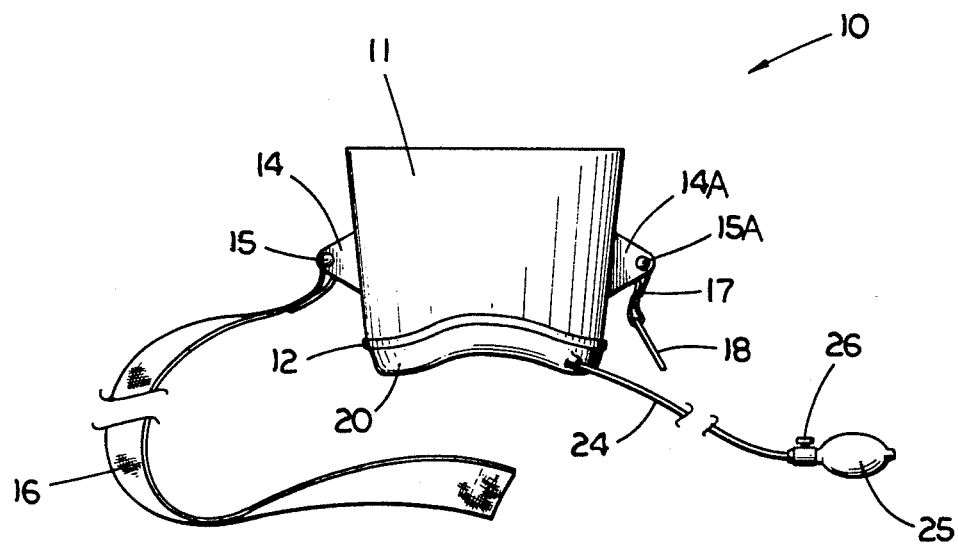
FIG. 1 is a side elevational view of a single breast direct water coupling device of the present invention.
Figure 2:
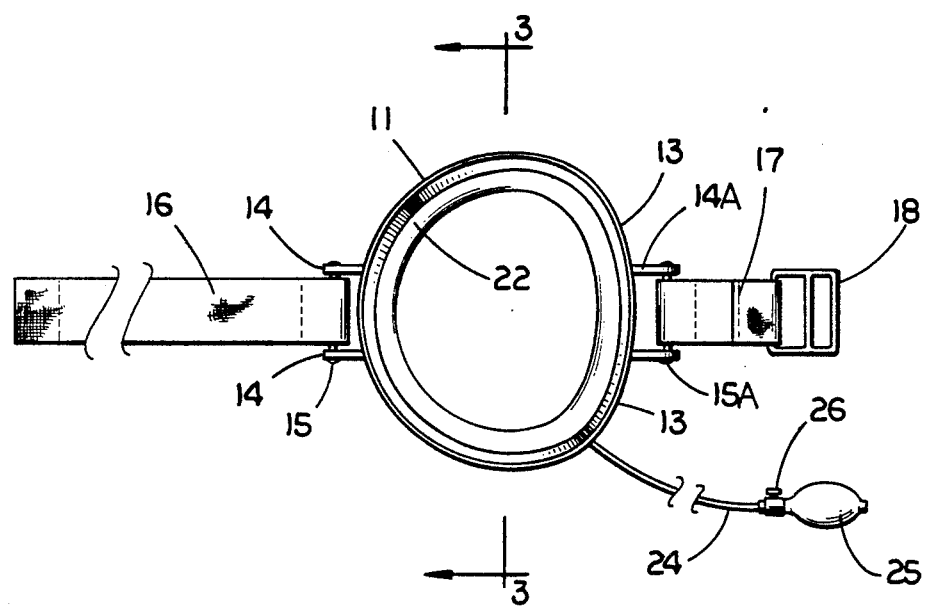
FIG. 2 is a top plan view of the direct water coupling device of FIG. 1.

The preferred embodiment of the present invention is illustrated in FIGS. 1 and 2. Direct water coupler 10 has a water retaining wall 11 which defines an enclosure. Wall 11 retains water within the direct water coupler 10 when the direct water coupler is mounted in position about the breast area of a human body.

Wall 11 may be made of any suitable material which retains water; however, it is preferable that wall 11 be of lightweight construction for convenience in handling and comfort to the patient when the device is in use. Also, in the preferred embodiment, wall 11 is made of transparent material so that the operating technician has a good view of the breast area during the scanning process. Wall 11 has a generally frustoconical shape, defining a larger opening at its top than at the bottom. This feature provides the operating technician with additional room to manipulate the ultrasound transducer without diminishing the stability of the coupler. It is also preferred that wall 11 be sufficiently rigid to retain water without stretching and to transfer downward pressure to the latex tubing 20 which is applied by strapping apparatus 14 through 18 when coupler 10 is in position. The downward pressure can be applied by a counter balanced arm or a similar device which applies a downward pressure to wall 11.

The bottom edge 12 of wall 11 is shaped so as to conform to the shape of a human body about the perimeter of the breast area. Latex tubing 20 is sealingly attached to the bottom edge 12 of wall 11. Latex tubing 20 is inflatable by air pump 25 which connects with latex tubing 20 through tube 24. Release valve 26 allows latex tubing 20 to deflate after use. When coupler 10 is mounted in position, latex tubing 20 is juxtaposed to the body about the perimeter of the breast area and provides a sealing relationship between wall 11 and the perimeter of breast area 30 of the patient. The inflation of latex tubing 20 further assures a good seal. Although inflatable latex tubing 20 is used in the preferred embodiment, any pressure pliable but water impervious material, which does not cause undue irritation to the skin tissue of the patient because of the applied pressure, its chemical make-up, or its surface characteristics, may be sufficient. Latex tubing is preferred because it has a soft enough texture so that it does not irritate the patient's skin tissue. It is also preferred that tubing 20 be sufficiently wide to avoid excessive pressure upon the patient. Closed cell foam materials have been successfully used (in place of the latex) by the inventors of this patent application.

On opposite sides of wall 11 are attaching mounts 14 and 14A to which straps 16 and 17 are respectively connected. Straps 16 and 17 are connected to attaching mounts 14 and 14A respectively by being looped about themselves and around rods 15 and 15A, respectively. Strap 17 has at its opposite end attached to it buckle 18. When coupling device 10 is mounted in position about the perimeter of the breast area, strap 16 wraps around the back of the patient and attaches to buckle 18. In this manner, the device is given stability and support when it is in position about the breast area of the human body. The attachment between strap 16 and buckle 18 can be adjusted to account for various body sizes of patients. Various types of pressure sensitive fastening fabric, such as Velcro-brand material, may be used for straps 16 and 17 as closing and holding devices in place of buckle 18.

In the preferred embodiment, strap 16 is three inches wide. It is preferrable that strap 16 be at least two inches wide so that the patient does not experience an excessive cutting pressure on her skin tissue. Attaching mounts 14 extend a distance laterally from wall 11 to ease pressure against the skin of the patient caused by strap 16.

Strapping apparatus 14 through 18 maintains coupler 10 in position about the breast area with latex tubing 20 sealingly juxtaposed to the body of the patient. In this manner, wall 11 can retain water within the enclosure defined by wall 11 when coupler 10 is in position about the breast. The support apparatus, as hereinabove described, is used in the preferred embodiment of the present invention for its simplicity and ease of use. Alternate support means could be incorporated and would still be within the spirit of the invention.

In FIG. 2, it can be seen that wall 11 has a generally circular appearance when viewed from above, with the exception that portion 13 of wall 11 is somewhat flattened in appearance. The preferred embodiment has this particular shape to account for the shape of the human body about the perimeter of the breast area. Portion 13 fits the contour of the human body to the outward side of the breast area.

Figure 3:
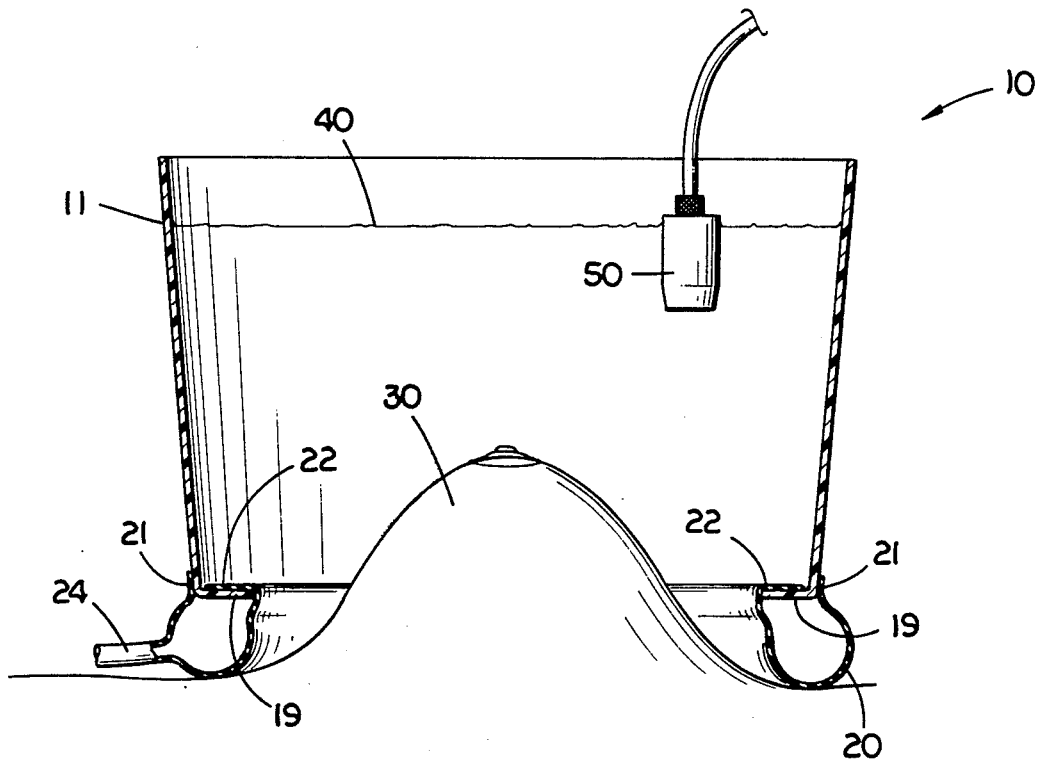
FIG. 3 is a fragmentary sectional view of the direct water coupler of FIGS. 1 and 2, mounted in position about a human breast with an ultrasonic transducer nearby. The sectional view is along line 3—3 of FIG. 2 and is viewed in the direction of the arrows.

FIG. 3 illustrates a sectional view of the preferred embodiment mounted about the perimeter of the breast area 30 of a patient. From the sectional view of FIG. 3 it can be seen that the bottom edge 12 of wall 11 has an inwardly directing flange 19. Latex tubing 20 is formed by a series of latex coatings which are cemented along the top portion 22 of flange 19 and the outside lower portion 21 of wall 11. Because tubing 20 is located directly below flange 19 and because of the rigidity of wall 11, when strapping apparatus 14 through 18 is tightened, downward pressure is evenly distributed about tubing 20 to aid in assuring a good seal.

Although different sizes of couplers are required in order to assure a proper seal for different sizes of patients, it is estimated that a collection of three sizes, small, medium, and large, will provide at least one size to adequately fit virtually any adult patient.

Also, while specific apparatus has been illustrated as a single breast coupler, a double breasted model equally falls within the scope of the present invention. A double breasted coupler is identical in concept to the above described single breasted coupler, except that the coupler extends about a breast area which includes both breasts of the patient. Therefore, where reference is made to a breast area, such should be interpreted as applying to the area of a single breast for the single breast coupler, and to both breasts for the double breasted version.

To use the above described apparatus, a patient is first placed in a supine position (lying upon her back). While the patient is in the supine position, direct water coupling device 10 is placed in position about the breast area of the patient, with latex tubing 20 in juxtaposition to the patient. In cases where the patient's skin is more sensitive than normal, it is preferred to rub the patient's skin with a jelly prior to placement of the coupling device. Strap 16 is brought around the back of the patient, is attached to buckle 18, and is tightened so that the coupling device is stably supported. Next, air pump 25 is operated to inflate latex tubing 20 in order to assure a good seal. Next, water 40 is placed in the interior of the direct water coupling device 10. As described, the coupling device being attached to the patient is movable with the patient and thereby movable relative to the ultrasound transducer 50 when the transducer is at a fixed position. The ultrasound breast scan is then performed using transducer 50. Either a standard circular disk type would be suitable for this application or any of the sector or linear array types of transducers.

During the breast scan, the breast area is readily accessible to the technician and thus repalpation of the breast and the making of fine adjustments in the scanning process are simple and easy to perform. Because the breast assumes a normal posture in the liquid environment, the scanning process can detect subtle alterations in structural components of the breast tissue which are the earliest sign of breast cancer.

During the scanning procedure, the breast can be visually inspected and either the patient's position or the transducer position can be adjusted to provide the best angle of sound entrance between the transducer and a tumor region. If there is any uncertainty during the scanning procedure regarding the precise location of a tumor, the breast may be repalpated and necessary adjustments made to provide the best angle for sound entrance. Such fine adjustments are normally not possible for patients examined in the prone or sitting forward position. Also, sound reflecting or sound attenuating markers may be placed at various points on the breast to act as reference points for locating tumors.

After the scan has been performed, water 40 may be removed by either using a suction system, a siphon system, ladeling the water out manually, or having the patient turn to her side to pour the water out into a receptacle. Alternately, a drain outlet can be incorporated at the base of the coupler.

The application of the above described apparatus is simple and easy to perform. The need for more complicated equipment and time consuming procedures is eliminated, while the breast area is readily accessible during the scanning procedure. The applied apparatus is comfortable to the patient, applying only a minimal amount of pressure against the skin of the patient in the sensitive areas near the breast, yet it does not present a problem of leakage while in place.

While there have been described above the principals of this invention in connection with specific apparatus and techniques, it is to be clearly understood that this description is made only by way of an example and not as a limitation to the scope of the invention.

What is claimed is:

1. A direct liquid coupler for ultrasound scanning with an ultrasound transducer means of a breast area of a patient in a supine position, said coupler comprising:
    (a) generally rigid wall means for maintaining a liquid within the breast area of the patient in a supine position, said wall means including a wall portion having an inside surface and an outside surface, the wall portion further defining a top opening and having a bottom edge portion, the bottom edge portion being contoured to conform to the shape of a human body about the periphery of a breast area including the curvature at the lateral chest wall area and the indentation of the breast bone area;
    (b) sealing means for sealing the wall portion to the patient about the periphery of the breast area, said sealing means including a seal attached to the bottom edge of the wall portion, the seal defining a bottom opening which is smaller than the top opening defined by the wall portion, the seal including a pliable, water impervious material; and
    (c) attachment means for attaching the wall portion directly to the patient to be supported by the patient so as to be movable with the patient and thereby movable relative to said ultrasound transducer means when said transducer means is at a fixed position in a position about the breast area with the seal being sealingly juxtaposed to the patient's body about the periphery of the breast area, said sealing means including said attachment means holding the seal tightly against the patient to provide a liquid tight seal.

2. The coupler of claim 1 in which said attachment means includes an adjustable strap connected at its ends to opposite outside surfaces of said wall portion, said adjustable strap being at least two inches wide and adjustable to a length that is sufficient to wrap around the back of a patient when said wall portion is in a position about a breast area of a human body in which said sealing means is juxtaposed to the body about the periphery of the breast area.

3. The coupler of claim 1 in which said wall portion has a generally frustoconical shape.

4. The coupler of claim 1 in which said sealing means includes an inflatable tube.

5. The coupler of claim 4 in which said inflatable tube includes latex material.

6. The coupler of claim 1 in which said sealing means includes a closed cell foam.

7. The coupler of claim 1 in which said bottom edge includes a radially inwardly directly flange.

* * * * *